United States Patent [19]

Seki

[11] Patent Number: 4,620,452
[45] Date of Patent: Nov. 4, 1986

[54] LIQUID SAMPLE INJECTING APPARATUS

[75] Inventor: Hideo Seki, Ibaraki, Japan

[73] Assignee: Hitachi, Ltd., Tokyo, Japan

[21] Appl. No.: 774,472

[22] Filed: Sep. 10, 1985

[30] Foreign Application Priority Data

Sep. 21, 1984 [JP] Japan .................. 59-199255

[51] Int. Cl.$^4$ ............................................ G01N 35/04
[52] U.S. Cl. ................................................. 73/864.21
[58] Field of Search ........... 73/864.21, 864.22, 864.85, 73/864.86, 61.1 C; 277/117

[56] References Cited

U.S. PATENT DOCUMENTS

| 3,529,475 | 9/1970 | Lightner et al. | 73/864.21 X |
| 3,530,721 | 9/1970 | Hrdina | 73/864.21 |
| 3,552,441 | 1/1971 | Luhleich | 73/864.86 X |
| 3,918,913 | 11/1975 | Stevenson et al. | 73/864.21 X |
| 4,094,195 | 6/1978 | Friswell et al. | 73/864.21 |
| 4,476,734 | 10/1984 | Banks et al. | 73/864.21 X |
| 4,478,095 | 10/1984 | Bradley et al. | 73/864.21 |
| 4,558,603 | 12/1985 | Chlosta et al. | 73/864.21 |

OTHER PUBLICATIONS

Japanese Unexamined Pub. No. 36791/79.
Japanese Unexamined Pub. No. 134494/78.

Primary Examiner—Stewart J. Levy
Assistant Examiner—Joseph W. Roskos
Attorney, Agent, or Firm—Antonelli, Terry & Wands

[57] ABSTRACT

A liquid sample injecting apparatus wherein a liquid sample is drawn by suction when a sample needle is moved to a lower position and the liquid sample drawn by suction is fed into a chromatographic column by using a carrier solvent when the sample needle is moved to an upper position. The apparatus is provided with seal members capable of providing a satisfactory seal to the outer peripheral surface of the sample needle by utilizing the high pressure of the carrier solvent when the carrier solvent is allowed to flow through the bore of the needle. When the sample needle is moved between the two positions, the high pressure of the carrier solvent applied to the outer peripheral surface of the sample needle is removed to reduce the frictional resistance offered to the outer peripheral surface of the sample needle, to thereby facilitate the movement of the sample needle.

4 Claims, 1 Drawing Figure

U.S. Patent
Nov. 4, 1986
4,620,452
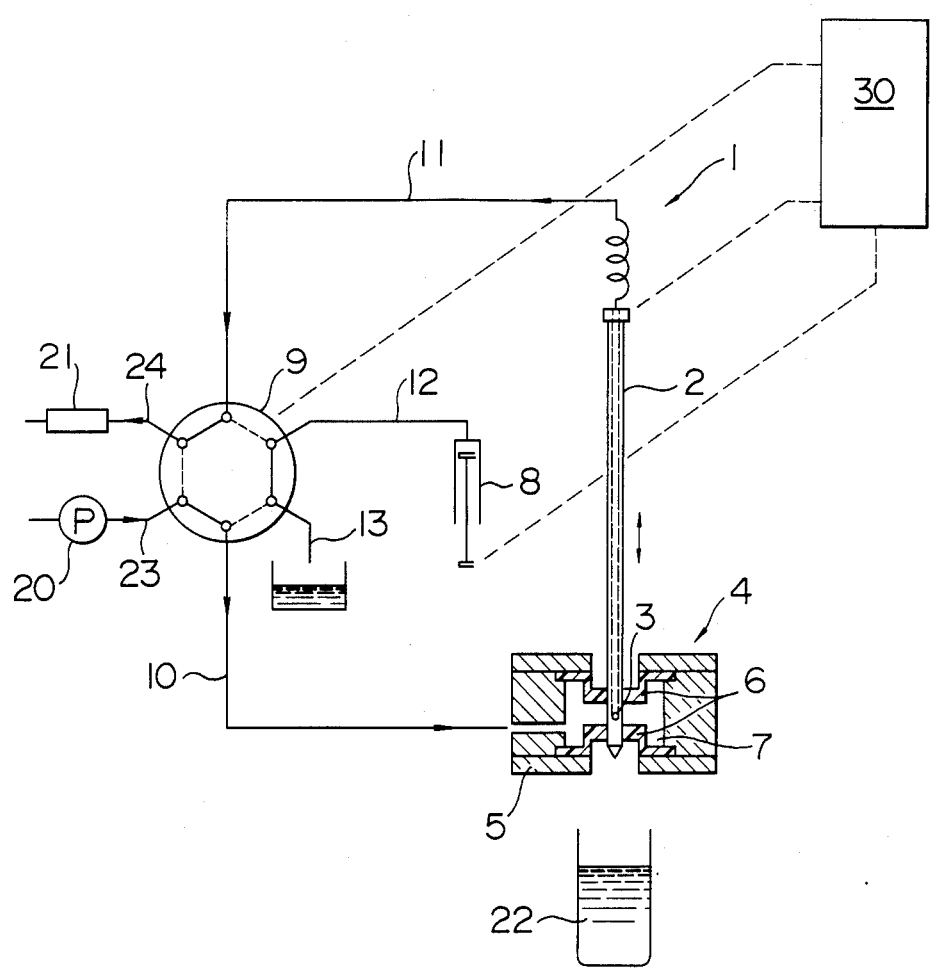

LIQUID SAMPLE INJECTING APPARATUS

BACKGROUND OF THE INVENTION

This invention relates to liquid sample injecting apparatus suitable for use in performing liquid chromatography, and more particularly to seal means for an outer peripheral surface of a sample needle of the liquid sample injecting apparatus.

A liquid sample injecting apparatus for successively introducing a multiplicity of kinds of liquid samples into a column in performing liquid chromatography is disclosed in U.S. Pat. No. 4,094,195, for example. When liquid chromatography is performed by using this apparatus, the method used comprises a step of drawing a liquid sample into a sample needle, and a step of feeding the liquid sample into the column by using a carrier solvent, the two steps being followed alternately. To this end, the sample needle is constructed such that it moves in sliding movement in an axial direction so that a hole at a forward end portion of the sample needle enters a liquid sample containing vessel to draw the liquid sample when brought to one position, and is then brought into communication with a passageway for the carrier solvent when brought to another position. Advances in the technology for the column have resulted in an increase in the resistance offered by its filter, causing the pressure of the carrier solvent to rise to over 5000 psi. This has raised a problem with regard to a seal around an outer peripheral surface of the sample needle at a connection of the needle with the carrier solvent passageway. The document referred to hereinabove discloses seal means comprising two sleeves formed of fluorocarbon-based material and serving as seal members located on the outer peripheral surface of the sample needle in a manner to hold the carrier solvent passageway between them, and a stress ring having a beveled deforming surface for mechanically compressing the sleeves from opposite sides of the length thereof so as to deform the sleeve radially inwardly to provide a positive seal to the outer peripheral surface of the sample needle. The seal means of this construction is considered to be able to provide a satisfactory seal. However, this seal means would be considered to suffer the following disadvantages. Since the sleeves press against the outer peripheral surface of the sample needle at all times, enhanced resistance would be offered to the sliding movement of the needle, and the service life of the sleeves would be short.

SUMMARY OF THE INVENTION

This invention has been developed for the purpose of obviating the aforesaid disadvantages of the prior art. Accordingly, the invention has as its object the provision of seal means which is capable of satisfactorily providing a seal when a liquid sample is introduced into the column by using a carrier solvent of high pressure, and also of reducing the resistance offered to the sliding movement of the sample needle to prolong the service life of the seal members.

The aforesaid object can be accomplished by utilizing the high pressure of the carrier solvent to cause the seal members to press against the sample needle and releasing the high pressure when the sample needle is moved axially. The seal means according to the invention is simple in construction and easy to operate.

BRIEF DESCRIPTION OF THE DRAWING

The single drawing is a schematic view of the liquid sample injecting apparatus incorporating therein the seal means comprising one embodiment of the invention.

DETAILED DESCRIPTION OF THE PREFERRED EMBODIMENT

A preferred embodiment will now be described by referring to the accompanying drawing. A liquid sample injecting apparatus 1 receives a carrier solvent pressurized by a high-pressure pump 20 via a passageway 23, and transfers the carrier solvent or a liquid sample to a chromatographic column 21 via a passageway 24. The liquid sample injecting apparatus 1 comprises a sample needle 2, a connection 4, a syringe 8, a six-way valve 9 and lines 10, 11, 12 and 13 connecting the devices 2, 4, 8 and 9 together. The sample needle 2 which is hollow is connected at its one end to one port of the six-way valve 9 via line 11, and has at the opposite end an opening 3 which is open transversely. The sample needle 2 extends through the connection 4 and moved vertically therethrough by a drive, not shown. The connection 4 comprises a housing 5 formed by assembling members formed of stainless steel, and two seal members 6 firmly secured to the housing 5, the housing 5 and seal members 6 cooperating with each other to define a pressure chamber 7. Each seal member 6 comprises a disc-shaped portion formed in a central portion thereof with an opening for the needle 2 to extend therethrough, a cylindrical portion contiguous with the disc-shaped portion and extending axially of the needle 2 toward an outer portion of the pressure chamber 7, and an annular flange portion extending radially outwardly from an outer end of the cylindrical portion. The seal members 6 are secured at the flange portions thereof to the housing 5 and face each other axially to define the pressure chamber 7 therebetween. The pressure chamber 7 is maintained in communication via a duct formed in one wall of the housing 5 with line 10 which is connected to the six-way valve 9. The seal members 6 formed of relatively flexible material, such as fluorine resin, function in such a manner that, when a carrier solvent of high pressure is present in the pressure chamber 7, the high pressure acts on an outer peripheral surface of the cylindrical portion of each seal member 6 so as to press peripheral edges of the disc-shaped portions inwardly and to deform the disc-shaped portions. The result of this is that inner peripheral surfaces of the disc-shaped portions defining the central openings are urged inwardly into intimate contact with an outer peripheral surface of the sample needle 2, to thereby provide a satisfactory seal to the connection 4.

Operation of the liquid sample injecting apparatus of the aforesaid construction will now be described. The sample needle 2 is moved upwardly to a position in which the opening 3 at the lower end of the needle 2 is communicated with the pressure chamber 7 of the connection 4. Then, the six-way valve 9 is brought to a solid line position shown in the drawing. A carrier solvent fed by the pump 20 via the passageway 23 is introduced through the six-way valve 9 into line 10, from which it flows through the opening 3 of the sample needle 2, an axial bore of the needle 2, line 11 and back to the six-way valve 9, from which it flows through the passageway 24 to a column 21. While the carrier solvent flows through the aforesaid path, the interior of the sample needle 2 is washed. Thereafter, the six-way valve 9 is switched to a phantom line position shown in the drawing to allow the carrier solvent fed via the passageway 23 and six-way valve 9 to be led to the passageway 24, from which it is introduced into the column 21. The line 10 connected to the pressure chamber 7 of the connection 4 is connected to a discharge line 13 in the six-way valve 9, so that the pressure of the carrier solvent in the pressure chamber 7 drops to an atmospheric pressure level.

Then, the sample needle 2 is moved downwardly to a position in which the lower end of the needle 2 enters a sample vessel. At this time, the pressure in the pressure chamber 7 has already dropped to the atmospheric pressure level, so that the seal members 6 press against the outer peripheral surface of the sample needle 2 with a pressure of low magnitude to allow the needle 2 to move downwardly readily with no great frictional resistance. Then, a sample in the sample vessel is drawn by suction into the needle 2 by means of a syringe 8, and the needle 2 is moved upwardly back to the position in which the opening 3 at the lower end of the needle 2 is brought into communication with the pressure chamber 7 in the connection 4. By returning the six-way valve 9 to the solid line position shown in the drawing, it is possible to cause the carrier solvent to flow through the passageway 23 and line 10 to push the sample that has been drawn into the needle 2, so that the sample flows through the line 11, six-way valve 9 and passageway 24 to the column. The carrier solvent in the syringe 8 is discharged via lines 12 and 13, to be ready for drawing another sample.

The process steps described hereinabove are repeatedly performed with regard to various kinds of samples. Usually, switching the six-way valve 9, moving the sample needle 2 upwardly and downwardly and operating the syringe 8 are automatically controlled by control unit 30 in timed relation.

In the embodiment shown and described hereinabove, the seal members 6 of the connection 4 are each annular in shape and substantially in the form of a letter Z in cross section. However, the invention is not limited to this specific form of the seal members, and it will be understood that any seal member of annular shape formed in a central portion thereof with an opening to allow the needle to extend therethrough is capable of providing a seal satisfactorily to the outer peripheral surface of the needle by the action of the high pressure in the pressure chamber, so long as a surface of the seal members in contact with a carrier solvent at which the carrier solvent is located radially outwardly of the seal members is greater in area than a surface of the seal members in contact with the carrier solvent at which the carrier solvent is located radially inwardly of the seal members. It will be appreciated that various changes and modifications may be made in the form of the seal members under the aforesaid conditions by those who have an ordinary skill in the art to which the invention relates.

From the foregoing description, it will be appreciated that the liquid sample injecting apparatus according to the invention enables a positive seal to be provided satisfactorily to the outer peripheral surface of the sample needle when the carrier solvent is made to flow through the interior of the needle, and that no great resistance is offered to the movement of the needle between its different positions, thereby enabling the service life of the seal members to be prolonged.

What is claimed is:

1. In a liquid sample injecting apparatus comprising a sample needle movable between a lower position in which a liquid sample is drawn by suction into the sample needle and an upper position in which the liquid sample is injected into a column, connection means for introducing a carrier solvent into the sample needle, and valve means for switching the direction of flow of the carrier solvent, the improvement wherein:

said connection means comprises a housing member and a pair of seal members defining a pressure chamber, each said seal member being annular in shape and formed in a central portion thereof with an opening allowing the sample needle to extend therethrough; and a surface of the seal members in contact with the carrier solvent at which the carrier solvent is located radially outwardly of the seal members is greater in area than a surface of the seal members in contact with the carrier solvent at which the carrier solvent is located radially inwardly of the seal members, whereby the seal members are forced, when a high pressure of the carrier solvent is present in the pressure chamber, by the high pressure of the carrier solvent to press against the sample needle so as to positively provide a seal to an outer peripheral surface of the sample needle, and the high pressure of the carrier solvent in the pressure chamber is removed therefrom, when the sample needle is to be moved, by actuating the valve means to reduce the pressure applied by the seal members to the sample needle.

2. A liquid sample injecting apparatus is claimed in claim 1, wherein each said seal member comprises a disc-shaped portion having an opening in the central portion for the sampling needle to extend therethrough, a hollow cylindrical portion extending from one side thereof toward an outer portion of the pressure applying chamber, and an annular flange portion extending radially outwardly from an end of the cylindrical portion located opposite the end at which the cylindrical portion is connected to the disc-shaped portion, to fix the seal member in position.

3. A liquid sample injecting apparatus is claimed in claim 1, wherein said valve means is capable of simultaneously controlling the direction of flow of the carrier solvent and the communication between the sample needle and a syringe.

4. A liquid sample injecting apparatus is claimed in claim 1, wherein said seal members are formed of fluorine resin.

* * * * *